US007578295B2

(12) United States Patent
Kurrus

(10) Patent No.: US 7,578,295 B2
(45) Date of Patent: Aug. 25, 2009

(54) ENDOBRONCHIAL BLOCKING DEVICE HAVING A REPLACEABLE SNARE

(75) Inventor: Michael R. Kurrus, Ellettsville, IN (US)

(73) Assignee: Cook Critical Care Incorporated, Bloomington, IN (US)

( * ) Notice: Subject to any disclaimer, the term of this patent is extended or adjusted under 35 U.S.C. 154(b) by 591 days.

(21) Appl. No.: 11/250,693

(22) Filed: Oct. 11, 2005

(65) Prior Publication Data

US 2006/0090761 A1    May 4, 2006

Related U.S. Application Data

(60) Provisional application No. 60/619,487, filed on Oct. 15, 2004.

(51) Int. Cl.
*A61B 17/24* (2006.01)
(52) U.S. Cl. .................. 128/207.16; 600/120; 606/113
(58) Field of Classification Search ............ 128/200.14, 128/200.23, 203.12, 207.14, 207.16, 200.26, 128/200.16; 600/120; 606/113
See application file for complete search history.

(56) References Cited

U.S. PATENT DOCUMENTS

| | | | |
|---|---|---|---|
| 4,824,435 A | | 4/1989 | Giesy et al. |
| 4,988,356 A | * | 1/1991 | Crittenden et al. .......... 606/192 |
| 5,814,052 A | * | 9/1998 | Nakao et al. ................. 606/115 |
| 5,904,648 A | | 5/1999 | Arndt et al. |
| 5,964,223 A | | 10/1999 | Baran |
| 6,520,183 B2 | | 2/2003 | Amar |
| 6,645,205 B2 | * | 11/2003 | Ginn .......................... 606/41 |
| 6,669,643 B1 | | 12/2003 | Dubinsky |

* cited by examiner

*Primary Examiner*—Steven O Douglas
(74) *Attorney, Agent, or Firm*—Brinks Hofer Gilson & Lione

(57) ABSTRACT

An endobronchial blocker catheter for use in blocking a selected mainstem bronchus under guidance of a bronchoscope. The endobronchial blocker catheter comprises a tubular assembly and an elongated body that receives the tubular assembly. The tubular assembly comprises a tubular member and a loop disposed at a distal end of the tubular member. The loop is sized such that the bronchoscope is passable through the loop. The elongated body has a plurality of lumens therein, and an inflatable blocker balloon disposed about a distal portion of the elongated body. One of the lumens extends to an interior of the balloon to accomplish inflation of the balloon for retaining the blocker catheter in the mainstem bronchus, and another lumen is sized for receiving the tubular assembly in a manner such that the loop extends from a distal end of the elongated body. The blocker catheter is guided by the bronchoscope to the desired inflation site via the loop.

20 Claims, 5 Drawing Sheets

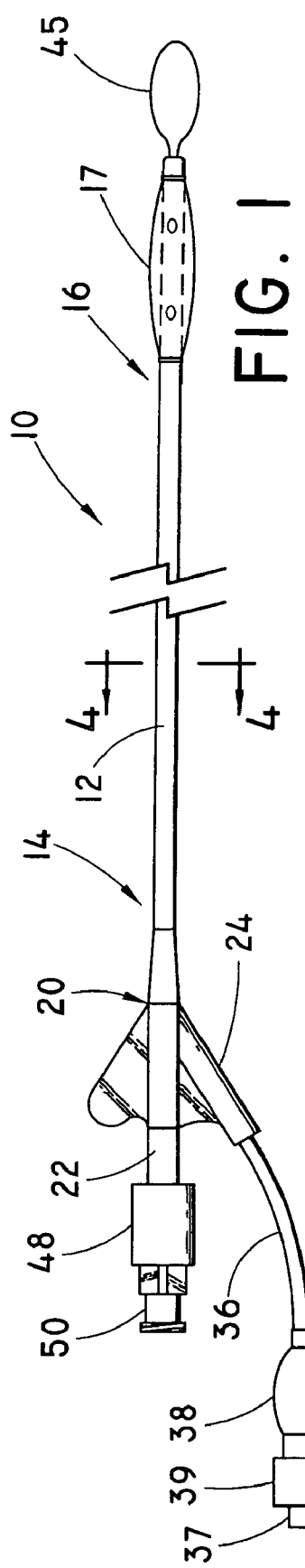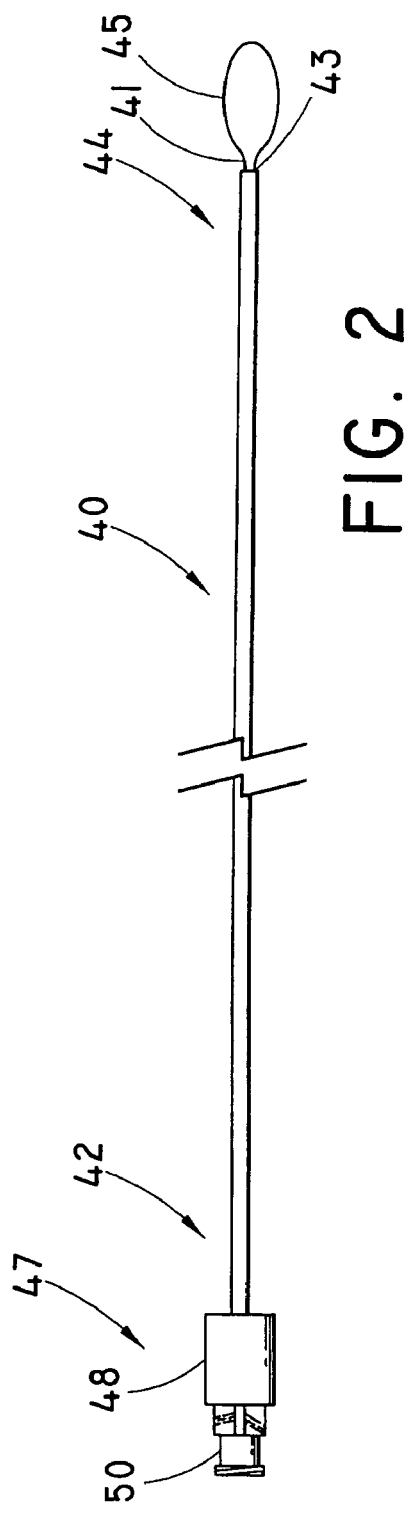

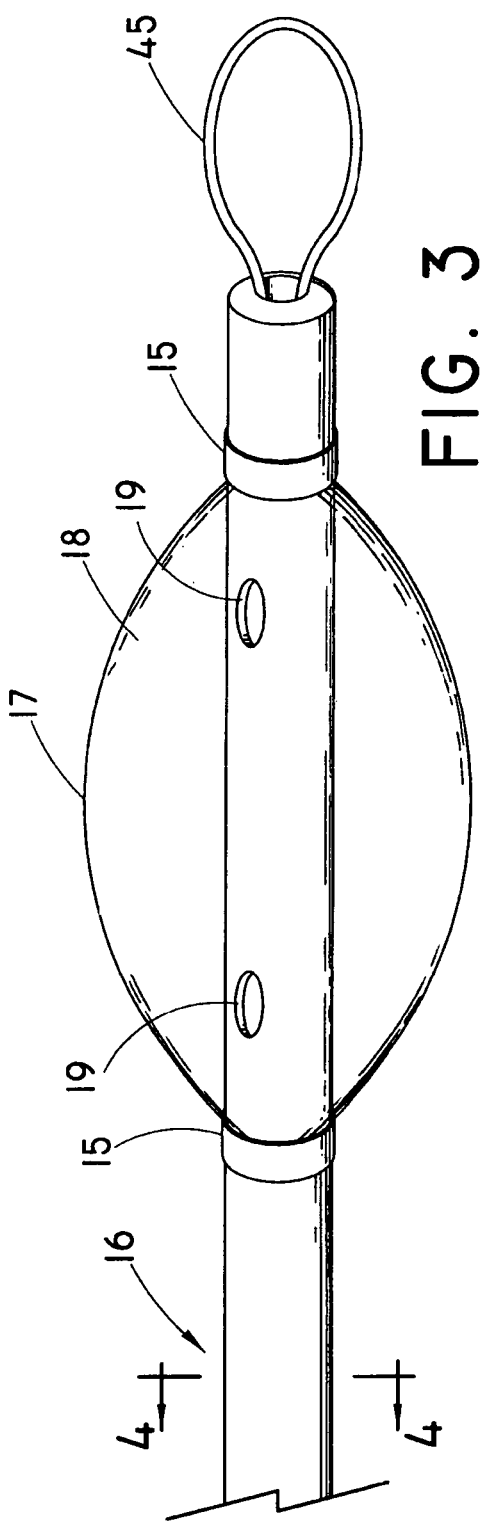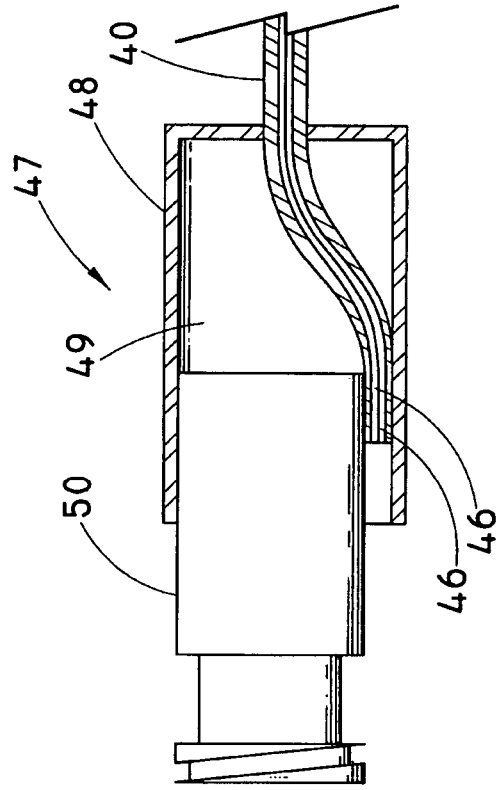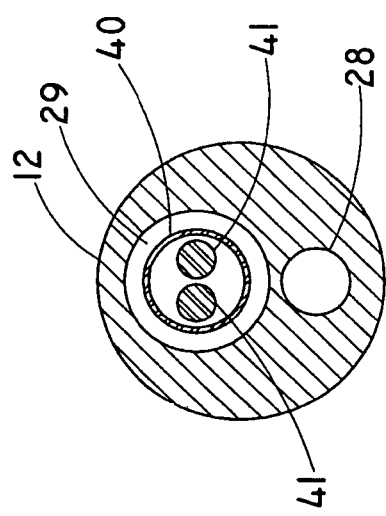

ENDOBRONCHIAL BLOCKING DEVICE HAVING A REPLACEABLE SNARE

RELATED APPLICATION

The present patent document claims the benefit of the filing date under 35 U.S.C. §119(e) of Provisional U.S. Patent Application Ser. No. 60/619,487, filed Oct. 15, 2004, which is hereby incorporated by reference.

BACKGROUND

1. Technical Field

The present invention relates generally to medical devices, and more particularly, to an endobronchial blocking device for use in isolating a lung or a portion of a lung.

2. Background Information

Patients who are critically ill or undergoing surgical procedures involving the lungs (thoracic surgery) frequently require a lung, or a portion of a lung, to be isolated from mechanical ventilation. The lungs are located in the chest cavity and bounded by the chest wall and the diaphragm, a thin muscular membrane. The lungs are held next to the chest wall by negative pressure and a thin fluid layer. The space of opposition is the pleural space. The lungs comprise the trachea, an air conduit, and the lung tissue which abuts against the chest wall. The trachea divides in the chest cavity into two separate air conduits, a right-sided air conduit (the right mainstem bronchus) and a left-sided air conduit (the left mainstem bronchus).

Ventilation is a physiologic process which supplies oxygen to the body and removes carbon dioxide, a gaseous waste product. Ventilation is provided by the rhythmic back and forth motion of air in the trachea, caused by the rhythmic contraction and relaxation of the diaphragm. In surgical patients and in the critically ill, ventilation can be assisted by utilizing a mechanical ventilator connected to an endotracheal tube. An endotracheal tube is a balloon-tipped single or double-lumen catheter that is open at both ends, and positioned in the mid-tracheal region.

Isolation of ventilation is commonly required in medical procedures. For example, in thoracic surgery the chest wall is incised, the lung opened and the pleural space entered. As a result, the lung will collapse, and ventilation can escape. Ventilation to the non-operative lung must be isolated before opening the operative lung segment. If ventilation is not isolated before beginning the thoracic surgery, a risk of harm to the patient exists due to the escape of ventilation through the surgical lung opening. Other conditions may also require isolation from mechanical ventilation. These conditions include the isolation of a diseased portion of the lung, infections of the lung (pneumonia), bleeding in the lungs (hemoptysis), and the presence of a non-surgical opening into the pleural space (pneumothorax).

Double lumen endotracheal tubes have long been used to achieve isolation of ventilation. A double lumen endotracheal tube generally comprises two endotracheal tubes of unequal length fused together, and incorporates two balloons. One balloon envelopes the tracheal position of the two fused endotracheal tubes (the tracheal balloon), and the second balloon envelopes the longer tube portion and extends into either the right or left mainstem bronchus (the bronchial balloon). The double lumen tube isolates ventilation when the balloons are inflated, and the longer tube portion is positioned in the right or left mainstem bronchus.

There are certain disadvantages associated with the use of double lumen endotracheal tubes. For example, a double lumen endotracheal tube is larger in outer diameter than a conventional single lumen endotracheal tube, yet its internal cross-sectional area is substantially the same as a single lumen tube. This extended outer diameter can cause damage to the vocal chords, as well as the nerves for the vocal chords. In addition, a larger diameter double lumen endotracheal tube is generally longer, and more challenging to insert and position than a single lumen tube. In patients where the normal airway anatomy is altered, the use of double lumen endotracheal tubes can result in additional patient trauma. Furthermore, due to the complexity and size of a double lumen endotracheal tube, hypoxic brain damage can occur as a result of the length of time that may be required to correctly place the device in the airway. Also, a double lumen endotracheal tube cannot be left in place for long periods of time. Due to its size, extended use of such a tube can cause damage to the tracheal bronchial tree.

Another known medical device for achieving isolation of ventilation is an endobronchial blocker. An endobronchial blocker is a balloon-tipped catheter which is positioned in either the right or left mainstem bronchus using a fiberoptic bronchoscope. When the device is properly positioned, the balloon is inflated to achieve isolation of ventilation. Some endobronchial blockers are not directly coupled to the motion of a fiberoptic bronchoscope. As a result, the operation of the fiberoptic bronchoscope and the balloon-tipped blocker are entirely independent, which can cause difficulty when positioning the blocker. Correct placement of such blockers normally requires several attempts before the device is properly positioned. Some of these devices utilize a removable stiff mandrel wire, placed in the lumen of the blocker, to allow manipulation during placement. The presence of such a wire can cause tissue trauma due to the stiffness of the end portion. In addition, such blockers only incorporate a single lumen in the design. This lumen accepts the removable mandrel wire, and allows inflation of the balloon when the mandrel wire is removed. The single lumen design can prevent gas from being properly aspirated from or added to the blocked section, irrigation fluids from being added to the blocked section, and irrigation fluid, secretions or blood from being removed from the blocked section. In addition, the balloon used with such devices is generally a low volume, low compliance, high pressure, spherical or elliptical balloon. This type of balloon can cause damage by transmitting excessive pressure to the tracheal wall, and it has no mechanism to sense the inflation pressure.

An improved endobronchial blocker is described in U.S. Pat. No. 5,904,648, incorporated by reference herein. The device of the '648 patent is a wire-guided double lumen blocker that has a nylon guide loop extending from a distal end-hole of the tube. The guide loop provides a mechanism to link the endobronchial blocker to a bronchoscope that is used to navigate the sharp bends of the tracheal bronchial tree. As a result, the blocker can be more easily guided to the desired location of a bronchial occlusion than earlier blockers. Following withdrawal of the bronchoscope and the loop, the balloon is inflated to provide obstruction of a portion of the lung from ventilation. This device has been found to be very effective in allowing accurate placement of the endobronchial blocker. However, if the blocker inadvertently becomes disengaged at some point during the medical procedure, it is generally not possible to reinsert the nylon guide loop, since the loop will generally buckle under the pushing reinsertion load. Thus, in order to reposition the blocker, it is necessary to repeat the entire insertion process with a new blocker. Although it would be possible to retain the guide loop in the bronchial mainstem throughout the procedure in order to simplify the possible re-positioning of the blocker, the maintenance of the guide loop occupies space in the lumen that is then not available for other uses, such as providing additional ventilation space to the patient. Thus, it is normally considered good practice to remove the guide loop during the blocking operation.

Yet another commercially available device that has been used to achieve isolation of ventilation is the UNIVENT tube. The UNIVENT tube is a double lumen endotracheal tube that includes a large lumen and a small lumen. The large lumen allows ventilation by conventional means, and the smaller lumen accepts an endobronchial blocker. The endobronchial blocker is advanced into the right or left mainstem bronchus, and the balloon is inflated to achieve isolation of ventilation. The remaining portion of the UNIVENT tube remains in the trachea in the same fashion as a conventional endotracheal tube. A disadvantage associated with the use of the UNIVENT tube is that the endobronchial blocker can be difficult to place, particularly in the left mainstem bronchus which requires that the blocker traverse a sharp angle. The tube should be placed using a fiberoptic bronchoscope; however the motion of the fiberoptic bronchoscope and the blocker are entirely independent. In addition, in clinical practice the UNIVENT tube is generally larger in diameter than a conventional endotracheal tube. This can lead to difficulty in tube placement, and to possible damage to the vocal chords. Furthermore, the ventilation lumen of the UNIVENT tube is smaller in cross-section than that of a similar-sized conventional endotracheal tube. In patients with severe pulmonary disease, this smaller cross-sectional area can make removal of the UNIVENT tube at the conclusion of surgery difficult. The effort involved in breathing through this small lumen is higher, and there is the risk of ventilatory failure.

It would be desired to provide an endobronchial blocking device that may be readily positioned via a fiberoptic bronchoscope in either the right or left mainstem bronchus, that may be used with a single lumen endotracheal tube, and that may be readily re-positioned in the bronchus in the event of dislodgement.

BRIEF SUMMARY

The present invention addresses the problems of the prior art. In one form thereof, the invention comprises an endobronchial blocker catheter comprising an elongated body and a tubular assembly receivable in the elongated body. The elongated body includes first and second lumens, and an inflatable blocker balloon disposed about a distal portion of the elongated body. The first lumen extends to an interior of the balloon to accomplish inflation, and the second lumen extends longitudinally through the elongated body. The tubular assembly is sized to be received in and extend substantially through the second lumen. The tubular assembly comprises a tubular member and a loop member disposed at a distal end of the tubular member. The tubular assembly is oriented with respect to the elongated body when the tubular assembly is received in the second lumen in a manner such that the loop member extends distally from a distal end of the elongated body.

In another form thereof, the present invention comprises an endobronchial blocker catheter for use in blocking a selected mainstem bronchus under guidance of a bronchoscope. The endobronchial blocker catheter comprises a tubular assembly and an elongated body that receives the tubular assembly. The tubular assembly comprises a tubular member and a loop disposed at a distal end of the tubular member. The loop is sized such that the bronchoscope is passable through the loop. The elongated body has a plurality of lumens therein, and an inflatable blocker balloon disposed about a distal portion of the elongated body. One of the lumens extends to an interior of the balloon to accomplish inflation of the balloon for retaining the blocker catheter in the mainstem bronchus, and another lumen is sized for receiving the tubular assembly in a manner such that the loop extends from a distal end of the elongated body, whereby the blocker catheter is guidable by the bronchoscope to the desired inflation site via the loop.

In still another form thereof, the present invention comprises a method for positioning an endobronchial blocker catheter in a selected mainstem bronchus of a patient under guidance of a tip-deflectable bronchoscope. In the inventive method, an endotracheal tube having a lumen therethrough is initially positioned in the trachea of a patient. An endobronchial blocker catheter is provided for insertion into the lumen of the endotracheal tube. The endobronchial blocker catheter comprises an elongated body having a plurality of lumens therein, and an inflatable blocker balloon disposed about a distal portion of the elongated body. A first lumen extends to an interior of the balloon to accomplish inflation of the balloon for retaining the blocker catheter in the mainstem bronchus. The elongated blocking catheter further comprises a tubular assembly comprising a tubular member and a loop disposed at a distal end of the tubular member. The tubular member is sized to be received in a second lumen, such that the loop extends from a distal end of the elongated body. The loop is sized such that the tip-deflectable bronchoscope is receivable therethrough. The tip-deflectable bronchoscope is passed through the loop, and the bronchoscope is advanced through the lumen of the endotracheal tube such that a distal end portion of the bronchoscope extends distally through the endotracheal tube into the selected mainstem bronchus. The blocker catheter is advanced via the loop along the bronchoscope to a desired site in the mainstem bronchus. The balloon is inflated such that the inflated balloon blocks the selected mainstem bronchus.

BRIEF DESCRIPTION OF THE DRAWINGS

FIG. 1 is a side elevational view of an endobronchial blocker catheter according to the present invention;

FIG. 2 is a side elevational view of a tubular member that extends through a lumen in the blocker catheter of FIG. 1;

FIG. 3 is an enlarged pictorial view of the distal portion of the endobronchial blocker of FIG. 1, with the balloon in an inflated state;

FIG. 4 is an enlarged cross-sectional view of the endobronchial blocker catheter taken along 4-4 of FIG. 3;

FIG. 5 is a side view, partially in section, of a connector assembly for connecting the tubular member to the endobronchial blocker catheter;

DETAILED DESCRIPTION OF THE DRAWINGS AND THE PRESENTLY PREFERRED EMBODIMENTS

Figure 6:
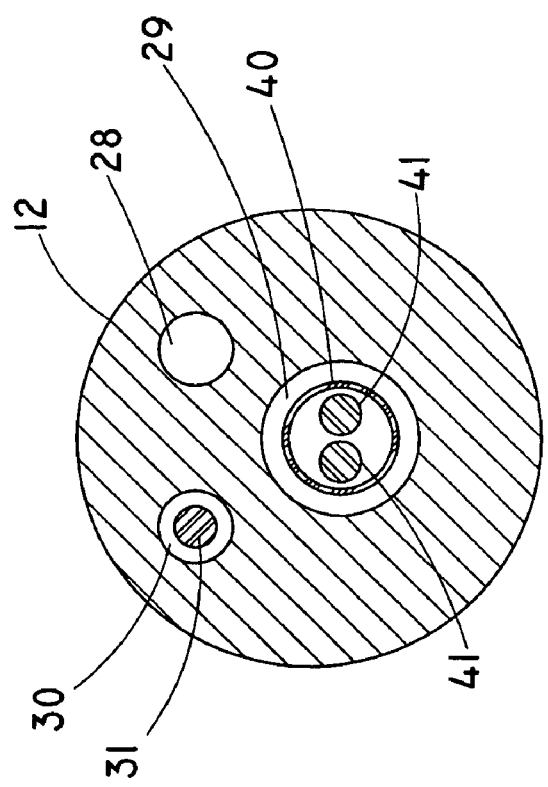
FIG. 6 is an alternative embodiment wherein the catheter includes three lumens.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated apparatus, and such further applications of the principles of the invention as illustrated therein being contemplated as would normally occur to one skilled in the art to which the invention relates.

FIG. 1 depicts a side elevational view of one embodiment of an endobronchial blocker catheter 10 of the present invention. In the following discussion, the terms "proximal" and "distal" will be used to describe the opposing axial ends of the apparatus, as well as the axial ends of various component features. The "proximal" end refers to the end of the endobronchial blocker catheter (or component thereof) that is closest to the operator during use of the assembly. The "distal" end refers to the end of the catheter (or component) that is initially inserted into the patient, or that is closest to the patient. In the orientation of endobronchial blocker catheter 10 and each of its component features shown in the figures herein, the proximal end is to the left of the page, while the distal end is to the right.

As shown in FIG. 1, endobronchial blocker catheter 10 includes an elongated blocker body 12 having a proximal end 14 and a distal end 16. An inflatable blocker balloon 17 disposed about a portion of the distal end. Catheter body 12 is preferably formed from a conventional pliable radiopaque plastic such as polyurethane, fluoroplastic, polyester, nylon, polypropylene or a silicone plastic. A conventional hub 20 is attached at proximal end 14. Hub 20 includes two extended portions 22, 24. Extended portion 24 is connected to one end of an inflation tube 36. A conventional inflation assembly, such as pilot balloon 38 and one-way valve 39, is provided at the other end of inflation tube 36 for receiving an inflation fluid through end 37 for use in inflating blocker balloon 17.

FIG. 2 depicts a side view of a flexible tubular member 40. When endobronchial blocker catheter 10 is fully assembled as shown in FIG. 1, tubular member 40 extends substantially through a lumen 29 (FIG. 4) in catheter body 12. Tubular member 40 is preferably formed from a flexible polymer such as the polyaryletherketone PEEK®, available from Victrex plc. Although tube 40 may be generally flexible, it should have at least sufficient stiffness to enable it be passed through lumen 29 without significant buckling or kinking.

A filament or wire 41, folded over on itself, extends in the distal direction from the proximal end 42 of tubular member 40 through the interior space of tubular member 40 until the axial end of the folded-over portion exits at end hole 43 of tubular member distal end 44 in the form of a loop, or snare, 45. The two axial ends of the folded-over wire are positioned generally at the proximal end of tube 40. Typically, wire 41 is formed from a conventional medical grade wire material, such as polymeric (e.g. nylon) monofilament. The diameter of wire 41 is generally dependent on the size of the endobronchial blocker. For example, for a 9 French blocker, the wire may have a diameter of about 0.327 mm (0.0128 inch).

Preferably, tubular member 40 includes a connector assembly 47 at proximal end 42 of tubular member 40. When the blocking catheter 10 is fully assembled, connector assembly 47 is affixed to the proximal end of hub extended portion 22 by conventional means, such as by providing internal threads on connector assembly 47 for connection to corresponding external threads on hub extended portion 22. Those skilled in the art will appreciate that other convenient attachment mechanisms can be substituted for the threaded connection described. As best illustrated in FIG. 5, connector assembly 47 can comprise a cap member 48 and an insert portion 50. Cap member 48 and insert portion 50 are sized relative to one another such that insert portion 50 is forcibly receivable in chamber 49 of cap member 48. Tubular member 40 is retained in connector assembly 47 by any suitable means, such as by compression between insert portion 50 and the inner wall of cap member 48. Similarly, the folded-over ends 46 of wire 41 may also be held by said compression or other suitable retaining means. Those skilled in the art will appreciate that other connection and retention mechanisms may be substituted for the mechanism shown and described, as long as the connection mechanism enables tubular member 40 to be securely maintained in connector assembly 47.

FIG. 3 illustrates an enlarged, pictorial view of distal portion 16 of endobronchial blocker catheter 10 of FIG. 1, showing inflatable blocker balloon 17 in an inflated state. Balloon 17 is made from a conventional elastomeric material, such as a silicone rubber material. Other conventional balloon compositions such as latex, polyurethane or silicone plastic may be substituted. The leading and trailing ends of balloon 17 are attached to elongated blocker body 12 at balloon attachment points 15 using, for example, a conventional medical grade adhesive. The balloon shown in FIG. 3 forms a generally elliptical shape when interior 18 of the balloon is inflated. During inflation, an inflation fluid from inflation assembly 38, 39 passes through inflation lumen 28 and communicates with the interior of balloon 17 through one or more exit ports 19 disposed in catheter body 12. Those skilled in the art will appreciate that other conventional balloon shapes, such as a spherical shape, a cylindrical shape, and the like, may be used in place of the elliptical shape illustrated in FIG. 3.

FIG. 4 illustrates an enlarged cross-sectional view of endobronchial blocker catheter 10 of FIG. 1 taken along line 4-4. In this embodiment, catheter body 12 includes two lumens 28, 29 therein. Lumen 28, comprising the balloon inflation lumen, extends substantially through catheter body 12. Lumen 28 is closed off at the distal end of body 12, causing lumen 28 to communicate only with interior 18 of balloon 17 through ports 19. As stated, the proximal end of lumen 28 communicates with inflation tube 36 and inflation assembly 38, 39. Large wire lumen 29 receives tube 40. As explained previously, tube 40 includes folded back wire 41 with the loop portion 45 extending from the distal end of the tube and with wire ends 46, 46 disposed at the proximal end of tube 40. Other features of the inventive endobronchial blocker catheter are similar in many respects to corresponding features in the incorporated-by-reference U.S. Pat. No. 5,904,648, and need not be further described here.

In an alternative embodiment, catheter body 12 may include a third lumen 30. This embodiment is shown in FIG. 6. In this embodiment, a conventional stiffening member, such as stiffening mandrel 31, may extend through some or all of the length of catheter body 12. Stiffening mandrels are well known in the art, and provide additional rigidity to all or a selected part of the length of a catheter.

Figure 7:
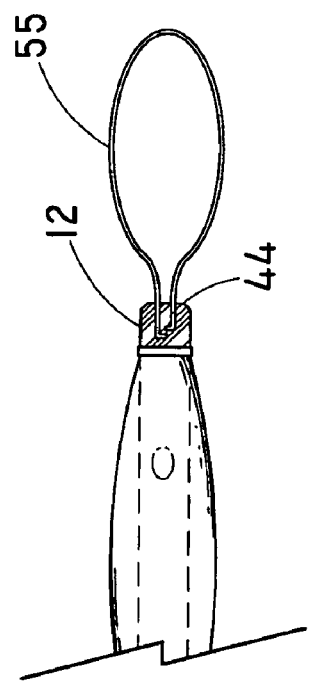
FIG. 7 is another alternative embodiment wherein the loop is affixed to and extends from the distal end of the catheter body.

Another alternative embodiment is illustrated at FIG. 7. In this embodiment, the wire is configured such that it forms a loop 55 that extends from tubular member distal end 44. Rather than comprising a wire 41 that is folded over to comprise the loop as described in previous embodiments, loop 55 is in the nature of a snare, and is simply bonded or otherwise adhered or affixed to distal end 44 of tubular member 40. In this way, it is not necessary to have a folded over wire that extends all the way through the tubular member. Accordingly, the tube in this embodiment need not include a separate wire lumen.

Figure 8:
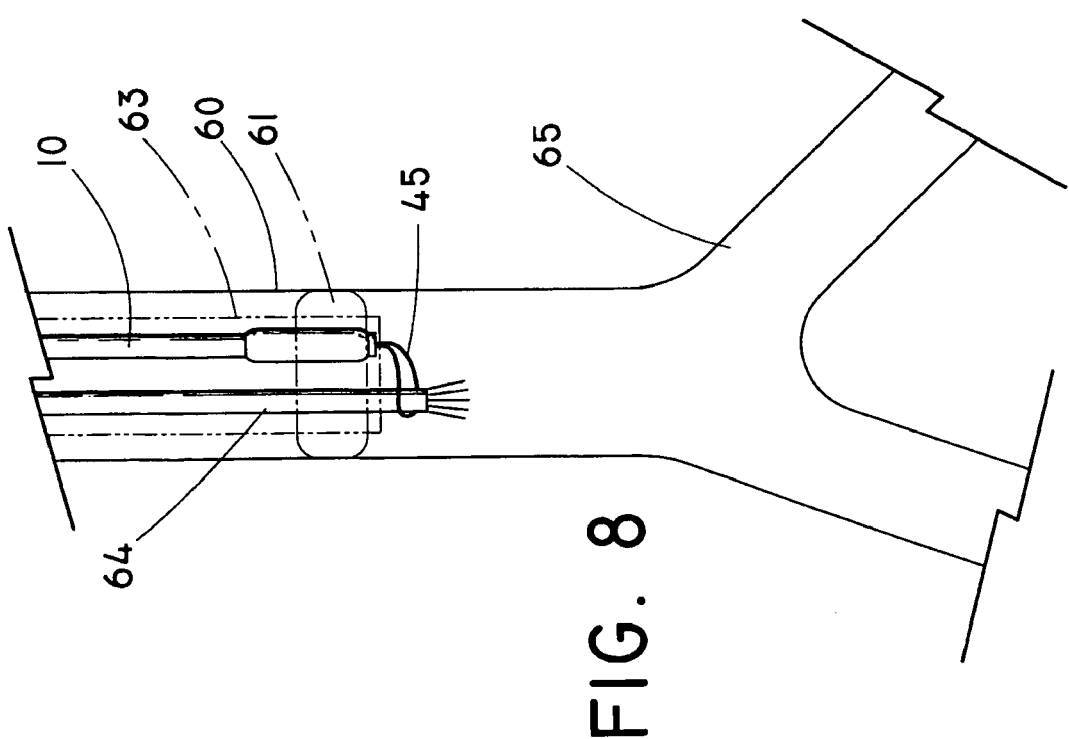
FIG. 8 is a profile view of a trachea with a bronchoscope passing through the wire loop of the endobronchial blocker catheter of FIG. 1.
Figure 11:
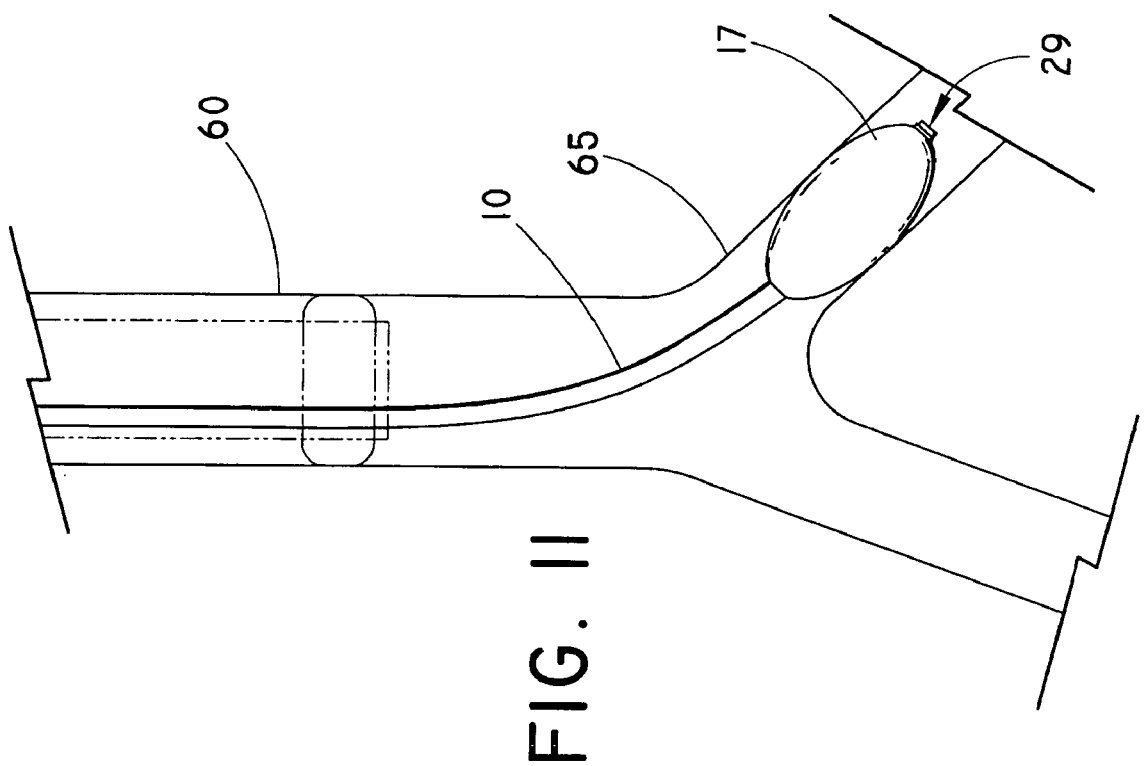
FIG. 11 is a profile view of the trachea with the endobronchial blocker catheter in left mainstem bronchus, the tubular assembly removed and the balloon inflated.

FIGS. 8-11 depict a preferred method of using the endobronchial blocker catheter 10. In FIG. 8, an endotracheal tube 63 with an inflated balloon 61 is positioned in the mid-tracheal region of the trachea 60 of a patient in conventional fashion. Preferably, a conventional multiport airway adapter such as the Arndt Multiport Airway Adapter, available from Cook Incorporated, of Bloomington, Ind., is used to coordinate the entry of the fiberoptic bronchoscope and the endobronchial blocker catheter into the endotracheal tube through separate ports of the multiport adapter.

Figure 9:
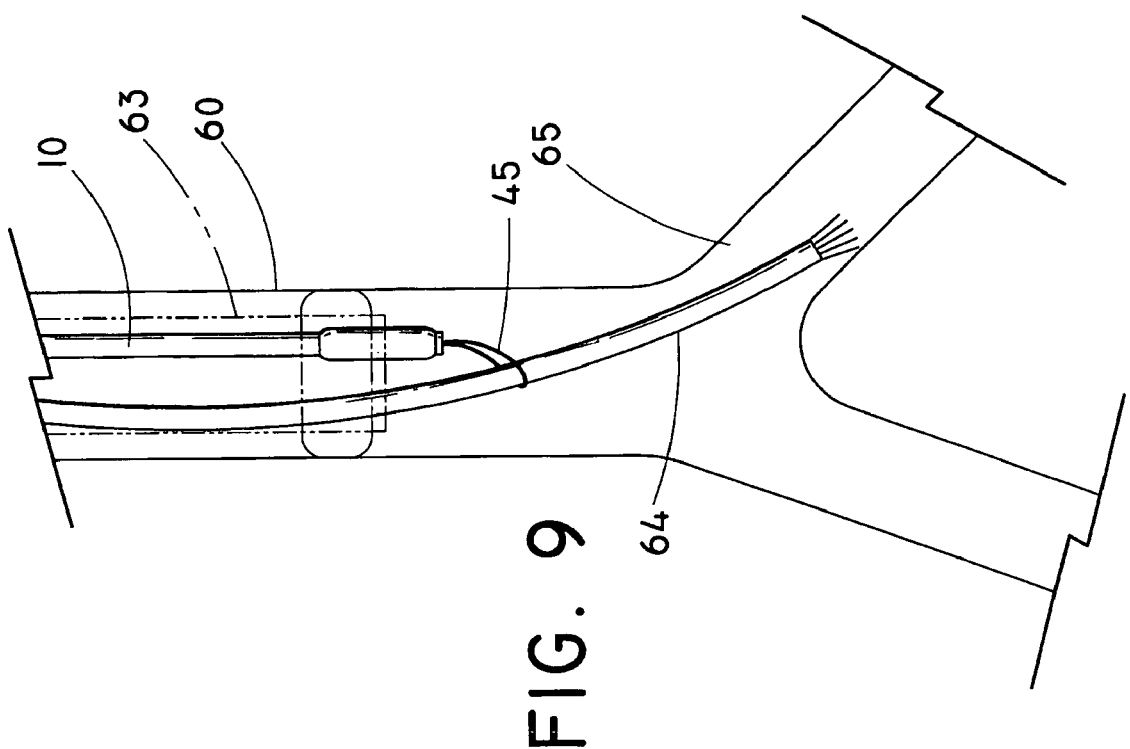
FIG. 9 is a profile view of the trachea with the bronchoscope advanced into the left mainstem bronchus of a patient.

A bronchoscope, such as fiberoptic bronchoscope 64, is advanced through the wire loop 45 of the endobronchial blocker catheter 10 by known means, such as by using the optics of the fiberoptic bronchoscope or using direct visualization through the clear plastic endotracheal tube. The bronchoscope incorporates a well-known, articulated tip control mechanism that permits continued visualization and navigation as it is advanced through the endotracheal tube to the desired location in the tracheo-bronchial tree. In FIG. 9, the bronchoscope 64 has entered the left mainstem bronchus 65. Without the direction provided by the fiberoptic bronchoscope, entry of the endobronchial blocker catheter into an area of the trachea with sharp bends, such as the left mainstem bronchus in particular, is problematic, difficult and time consuming. It is also potentially damaging to the trachea due to the multiple attempts it sometimes takes to gain entrance into the desired airway, and the repetitive collisions that may occur with the tracheal wall as the endobronchial blocker catheter is maneuvered to gain entrance into the desired airway passage.

Figure 10:
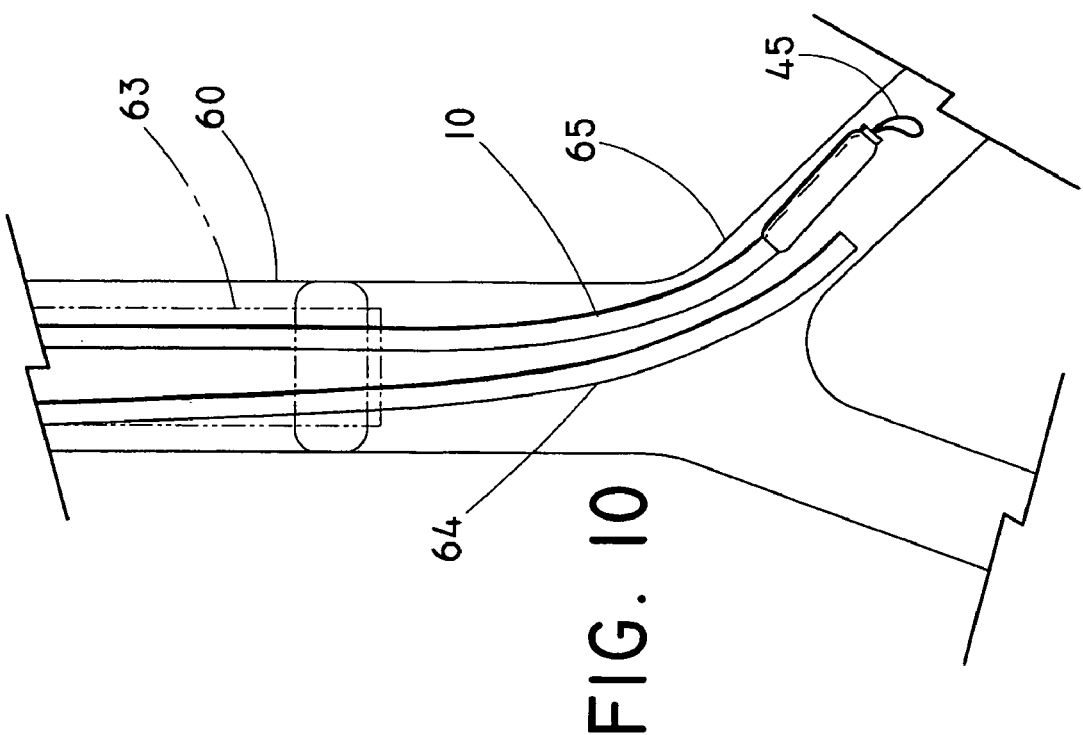
FIG. 10 is a profile view of the trachea with the endobronchial blocker catheter advanced off the bronchoscope into the left mainstem bronchus.

Once fiberoptic bronchoscope 64 has been maneuvered into position in the desired bronchus, the endobronchial blocker catheter 10 is advanced into the bronchus along the bronchoscope via the wire loop 45. In this way, the bronchoscope 64 acts as a guide for the catheter 10. The leading end of the catheter is then advanced further into the bronchus beyond the distal end of the bronchoscope, as shown in FIG. 10. Proper positioning of the distal end of the catheter may be visually confirmed through the fiberoptic bronchoscope.

Under continued bronchoscopic vision, the blocker balloon 17 is inflated to insure correct placement using the balloon inflation assembly as previously described. When fully inflated, balloon 17 should fill the entire endobronchial lumen to be blocked, and not herniate into the mainstem trachea. In most patients, the balloon will require between 6 and 12 ml of air to seal the lumen of the bronchus. Inflation of the balloon prevents ventilation from reaching the lung areas distal to the inflated balloon.

When correct placement has been confirmed, fiberoptic bronchoscope 64 is retracted. Preferably, the bronchoscope is initially pulled back behind the balloon, so that the physician can observe the inflation of the balloon. Once the physician is confident that the balloon has been properly inflated and positioned, the physician can thereafter remove the bronchoscope. The tubular member 40 and wire loop 45 can also be removed through lumen 29 of blocker elongated body 12. Tube 40 is preferably not withdrawn until this point so that the balloon can be re-positioned if necessary. With tube 40 withdrawn, the large endobronchial blocker lumen 29 allows communication from the sealed lung segment to the exterior of the blocker. A conventional adapter is preferably engaged with the proximal end of the lumen to facilitate hookup to a ventilator (not shown). Either fluid or gas can then be added or removed from the sealed lung segment as desired. Although the process could be carried out with the tube remaining in blocker lumen 29, the withdrawal of tube 40 (and the accompanying wire loop) is beneficial because it allows more area within lumen 29 to be available for the passage of fluid or gas.

On some occasions following placement of the endobronchial blocker catheter in the selected mainstem bronchus, the catheter may become dislodged from its position in the bronchus. This may occur, for example, when the patient is being repositioned following insertion of the endobronchial blocker catheter, but prior to surgery. In these instances, the endobronchial blocker catheter 10 is withdrawn through the endotracheal tube, and tube 40 having the projecting wire loop 45 is reinserted into catheter 10 through lumen 29 as before. The fiberoptic bronchoscope is then re-threaded through wire loop 45 as before, and the insertion process is repeated.

With prior art endobronchial blocker catheters it had not been possible to readily re-position the wire through the lumen once it had been withdrawn. In such cases, the wire did not have enough pushability to pass through lumen 29, and would generally buckle upon reinsertion. The use of tube 40 enables the physician to insert a stiffer structure through lumen 29 that does not buckle. As a result, the physician may simply reinsert the tube and wire through lumen 29, and re-position the endobronchial blocker catheter as before. This cuts down on the critical time that the patient is under anesthesia, and additionally, enables the physician to avoid the necessity of utilizing an entirely new blocker assembly.

It is therefore intended that the foregoing detailed description be regarded as illustrative rather than limiting, and that it be understood that it is the following claims, including all equivalents, that are intended to define the spirit and scope of this invention.

The invention claimed is:

1. An endobronchial blocker catheter, comprising:
an elongated body having first and second lumens therein and an inflatable blocker balloon disposed about a distal portion thereof, said first lumen extending to an interior of the balloon to accomplish inflation, and said second lumen extending longitudinally through said elongated body; and
a tubular assembly sized to be received in and extend substantially through said second lumen, said tubular assembly comprising a tubular member and a loop member disposed at a distal end of said tubular member, said tubular assembly oriented with respect to said elongated body when said tubular assembly is received in said second lumen such that said loop member extends distally from a distal end of said elongated body.

2. The blocker catheter of claim 1, wherein said tubular assembly comprises a wire extending at least partially through said tubular member, said wire defining said loop member.

3. The blocker catheter of claim 2, wherein said wire includes first and second ends, each of said ends extending to a proximal portion of said tubular assembly.

4. The blocker catheter of claim 1, wherein said tubular assembly comprises a connector assembly at a proximal end thereof for removable affixation to said elongated body.

5. The blocker catheter of claim 4, wherein said connector assembly includes threads sized and arranged on a surface of said tubular member for threaded engagement with complementary threads at a proximal end of said elongated body.

6. The blocker catheter of claim 1, wherein said elongated body comprises a third lumen, and wherein an elongated stiffening member extends through at least a part of said third lumen.

7. The blocker catheter of claim 1, wherein said loop member is affixed at said distal end of said tubular member.

8. The blocker catheter of claim 7, wherein said loop member is affixed at said distal end of said tubular member by at least one of bonding or adhering.

9. The blocker catheter of claim 1, wherein said loop member comprises a monofilament polymer.

10. An endobronchial blocker catheter for use in blocking a selected mainstem bronchus under guidance of a bronchoscope, comprising:
    a tubular assembly, said tubular assembly comprising a tubular member and a loop disposed at a distal end of said tubular member, said loop sized such that said bronchoscope is passable therethrough; and
    an elongated body having a plurality of lumens therein, and an inflatable blocker balloon disposed about a distal portion of said elongated body, a first one of said lumens extending to an interior of the balloon to accomplish inflation of said balloon for retaining said blocker catheter in said mainstem bronchus, a second one of said lumens sized for receiving said tubular assembly in a manner such that said loop extends from a distal end of said elongated body, whereby the blocker catheter is guidable by the bronchoscope to the desired inflation site via the loop.

11. The blocker catheter of claim 10, wherein said tubular assembly comprises a wire extending at least partially through said tubular member, said wire defining said loop.

12. The blocker catheter of claim 11, wherein said wire includes first and second ends, each of said ends extending to a proximal portion of said tubular assembly.

13. The blocker catheter of claim 10, wherein said tubular assembly comprises a connector assembly at a proximal end thereof for removable affixation to said elongated body.

14. The blocker catheter of claim 10, wherein said elongated body comprises a third lumen, and wherein an elongated stiffening member extends through at least a part of said third lumen.

15. The blocker catheter of claim 10, wherein said loop is affixed at said distal end of said tubular member.

16. The blocker catheter of claim 15, wherein said loop is affixed at said distal end of said tubular member by at least one of bonding or adhering.

17. A method for positioning an endobronchial blocker catheter in a selected mainstem bronchus of a patient under guidance of a tip-deflectable bronchoscope, comprising:
    positioning an endotracheal tube in the trachea of a patient, said endotracheal tube having a lumen therethrough;
    providing an endobronchial blocker catheter for insertion into the lumen of the endotracheal tube, said endobronchial blocker catheter comprising an elongated body having a plurality of lumens therein and an inflatable blocker balloon disposed about a distal portion of said elongated body, a first one of said lumens extending to an interior of the balloon to accomplish inflation of said balloon for retaining said blocker catheter in said mainstem bronchus; said elongated blocking catheter further comprising a tubular assembly comprising a tubular member and a loop disposed at a distal end of said tubular member, said tubular member received in a second one of said lumens such that said loop extends from a distal end of said elongated body, said loop being sized such that said tip-deflectable bronchoscope is receivable therethrough;
    passing said tip-deflectable bronchoscope through said loop, and advancing said bronchoscope through said lumen of the endotracheal tube such that a distal end portion of said bronchoscope extends distally through said endotracheal tube into the selected mainstem bronchus;
    advancing the blocker catheter via the loop along the bronchoscope to a desired site in said mainstem bronchus; and
    inflating said balloon such that said inflated balloon blocks the selected mainstem bronchus.

18. The method of claim 17, further comprising the steps of confirming placement of said endobronchial blocker through said bronchoscope, withdrawing said bronchoscope, and removing said tubular assembly through said second lumen of said blocker elongated body.

19. The method of claim 18, further comprising the step of withdrawing the endobronchial blocker catheter through the endotracheal tube, and reinserting the tubular assembly through second lumen.

20. The method of claim 19, further comprising the steps of passing said bronchoscope through said loop of said reinserted tubular assembly, re-advancing the blocker catheter via the loop along the bronchoscope to a desired site in said mainstem bronchus; and re-inflating said balloon such that said inflated balloon blocks the selected mainstem bronchus.

* * * * *

UNITED STATES PATENT AND TRADEMARK OFFICE
CERTIFICATE OF CORRECTION

PATENT NO.        : 7,578,295 B2
APPLICATION NO.  : 11/250693
DATED             : August 25, 2009
INVENTOR(S)       : Michael R. Kurrus It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 909 days.

Signed and Sealed this

Seventh Day of September, 2010

David J. Kappos
*Director of the United States Patent and Trademark Office*